United States Patent [19]

Cogez

[11] 4,448,501

[45] May 15, 1984

[54] EYE GLASSES FOR EXPERIMENTATION AND TESTING

[75] Inventor: Jean Cogez, Paris, France

[73] Assignee: Essilor International (Compagnie Generale d'Optique), Creteil, France

[21] Appl. No.: 367,958

[22] Filed: Apr. 13, 1982

[30] Foreign Application Priority Data

Apr. 13, 1981 [FR] France ................... 81 07359

[51] Int. Cl.³ .................. G02C 5/04; G02C 5/12; A61B 3/04
[52] U.S. Cl. ................... 351/128; 351/137; 351/227
[58] Field of Search ............... 351/128, 137, 227, 228, 351/229, 230, 231

[56] References Cited

U.S. PATENT DOCUMENTS 2,381,126 8/1945 Keller ..................... 351/227

Primary Examiner—John K. Corbin
Assistant Examiner—Rodney B. Bovernick
Attorney, Agent, or Firm—Burgess, Ryan & Wayne

[57] ABSTRACT

Eye glasses for experimentation and testing comprising a frame on which adjustable lens holders can be shifted.

They comprise a frontal mounting 1 which is extended downwardly in its central portion in the direction of the patient's nose by a bar 5 of short length and on which glides a vertically adjustable support 6 for engagement with the patient's nose or his regular eye glasses which the patient has to wear during the testing.

Application of the eye glasses for allowing tests to be taken with a patient who has to get new glasses with different corrective lenses and different positions of said lenses with respect to the eyes of the patient.

6 Claims, 6 Drawing Figures

EYE GLASSES FOR EXPERIMENTATION AND TESTING

BACKGROUND OF THE INVENTION

The present invention relates to eye glasses for experimentation and testing which are mainly utilized for measuring the refraction on one or both eyes of a patient.

Eye glasses for testing of the known type comprise screw-operated devices for the adjustment to the distance between the pupils and the adjustment in height, and they allow also the rotation of test lenses in their seats for determining the axes of astigmatism.

These eye glasses are adapted for adjustment to the head of the patient with the aid of a bridge and adjustable lenses as well as adjustable support means on the nose of the patient. The lense are adjustable by sliding on the bridge, with the sidepieces of the eye glasses either being pivoted at the bridge or on the frame holding the lenses. The support means for the nose are adjustably mounted either on the lens frame or at the transverse axis forming the bridge, and in certain modifications the bridge itself is formed of elements which are adjustable relative to each other either by telescoping or by sliding.

The test eye glasses presently used have several drawbacks, among which are: the fact that they are not at all esthetic, which discourages patients from wearing them for a lengthy test period; the manufacturing cost is high; the near-impossibility of testing multifocal or progressive lenses or lenses to be worn with eye glasses which the patient is already wearing.

SUMMARY OF THE INVENTION

One of the objects of the present invention is to obviate these shortcomings, while keeping the different kinds of adjustment which were explained and by using simpler, more esthetic and less onerous means.

For this purpose the eye glasses for experimentation and testing of this type comprise a frame on which adjustable lens carriers can be displaced to allow eye glass testing by a patient with different corrective lenses and different positioning of these lenses relative to the eyes of the patient. These eye glasses are characterized in that they comprise a frontal mounting provided with two sidepieces adapted to be placed substantially on the level of the eyebrows of the patient, and on which slide, longitudinally in an adjustable manner, two carriers, on each of which a lens holder is fixed, and in that the mounting is extended dowswardly in in its central portion in the direction of the nose of the patient by a bar of short length and on which slides a vertically adjustable support which comes to rest on the patient's nose and/or on the eye glasses which the patient has to wear during testing. The bar has a portion which is provided with two non-parallel faces which form a wedging bevel and which is engaged by two conjugate faces of the adjustable support under the action of an elastic means for maintaining the adjustable support in position by wedging. This elastic means is preferably a spring whose wedging action can be suppressed by the wearer's hand with which he adjusts the support position.

The spring can be an elastic leaf which is integral with the support and which engages a portion of the bar in such a manner that the wearer who is in the process of adjusting the support, can, by pressing on the support, suppress the wedging of the support on the inclinded faces. In an economical embodiment the leaf is an element which has been cast in one block, with the support being made of a relatively elastic material, such as a plastic material.

The support can comprise fixing means for several holding means adaptable to the nose and/or the eye glass frame which is already worn by the patient. The frontal mounting normally carries a gradation on which reference marks can be applied, with at least one set of markings on each carrier.

To assure the patient of esthetic comfort so as to persuade him to wear the eye glasses for experimentation and testing for an extended period, each of the carriers slides in a groove which is at least partly hidden at the inside of the frame, and the adjustable support is provided with rounded edges on all outer surfaces.

DESCRIPTION OF THE DRAWINGS

Other objects, advantages and features of the invention are set forth in a description of a preferred embodiment and in the attached drawing, of which.

DETAILED DESCRIPTION

Figure 2:
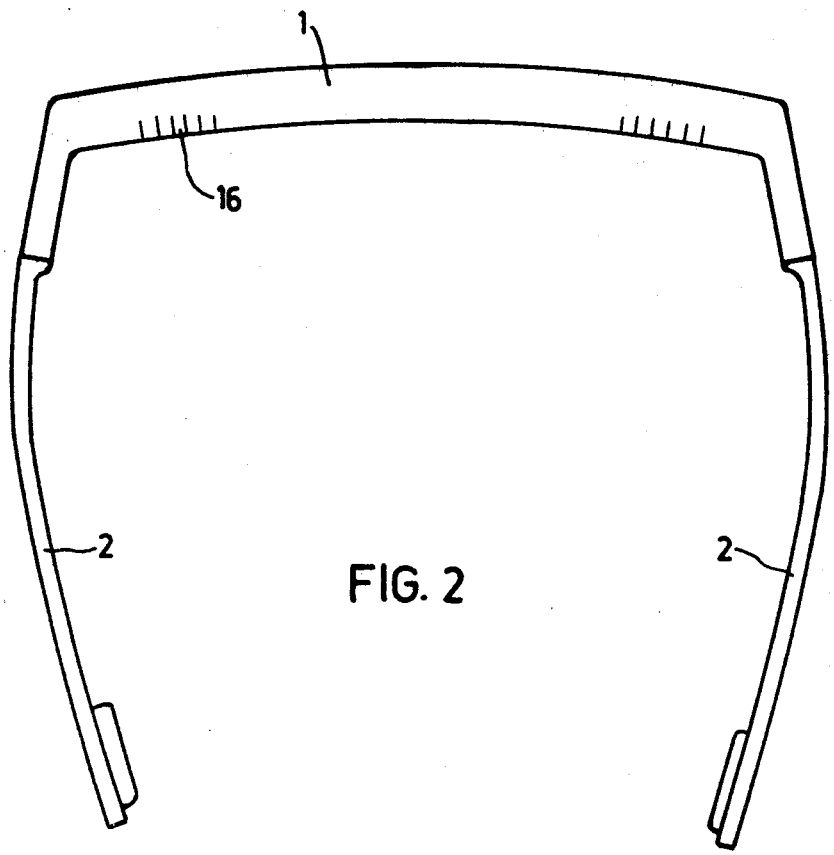
FIG. 2 is a top view showing its general outline.

The frame of the eye glasses for experimentation and testing as shown in FIG. 2 comprises a mounting 1 on which are fixed or articulated two sidepieces 2 of relatively great length so that they can be adapted to the heads of different wearers.

Figure 1:
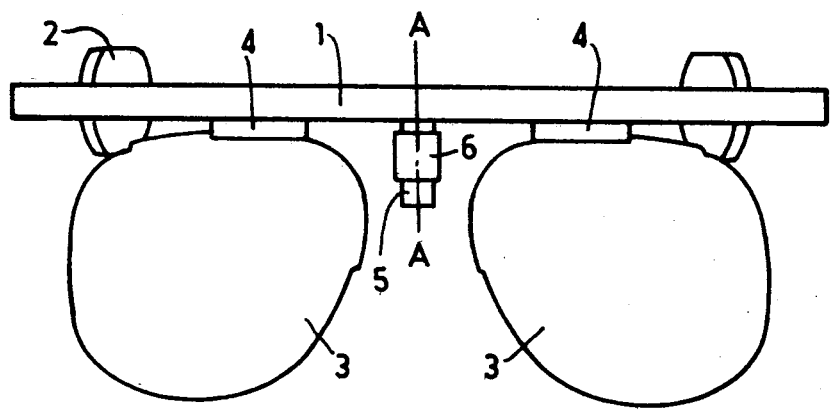
FIG. 1 shows a frontal view of an eye glass frame provided with lenses.

The mounting 1 as shown in FIG. 1 carries two test lenses 3, each of which is fixed in a lens holder 4 which is integral with a carrier sliding in a groove of the mounting. In its central portion the mounting 1 is extended downwardly in the direction of the patient's nose by a bar 5 which is relatively short and on which slides an adjustable support 6 which carries a removable holding piece 7 (see FIG. 3) which is engageable with the patient's nose, or, if he wears his regular eye glasses during the test, with the frame of the eye glasses already worn by him.

Figure 3:
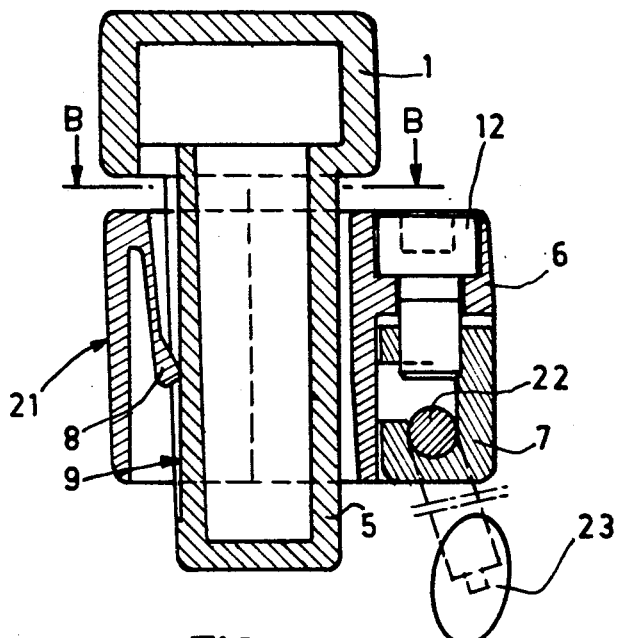
FIG. 3 is a sectional view of the mounting of the frame and its central bar having an adjustable support according to plane A in FIG. 1.
Figure 4:
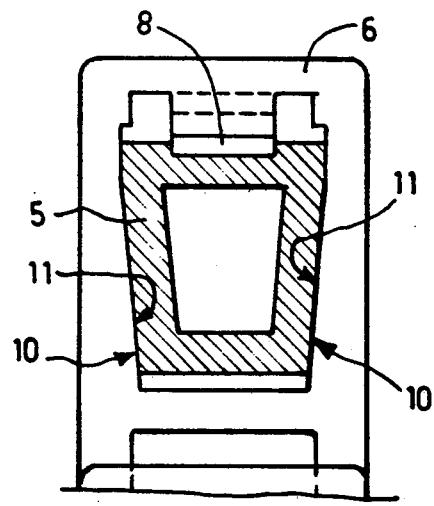
FIG. 4 shows the central bar and the support in section according to plane B in FIG. 3.

Bar 5 and adjustable support 6 are described in more detail and shown on an enlarged scale in FIGS. 3 and 4. The section of FIG. 3 shows that support 6 has an elastic leaf 8 which is made by integral casting with support 6 of plastic material and which is in elastic engagement on a face of bar 5. Leaf 8 is biased to bring back the two inclined faces 10, arranged in beveled form inside support 6, into contact with the two conjugated faces 11 of the area of bar 5, in such a manner as to wedge support 6 in position in that area of bar 5. The removable holding piece 7 which is attached to support 6 by any suitable means, such as a screw 12, is thus made integral with bar 5 and mounting 1 to allow an engagement of mounting 1 with the patient's nose or the eye glasses he wears during the test.

Figure 5:
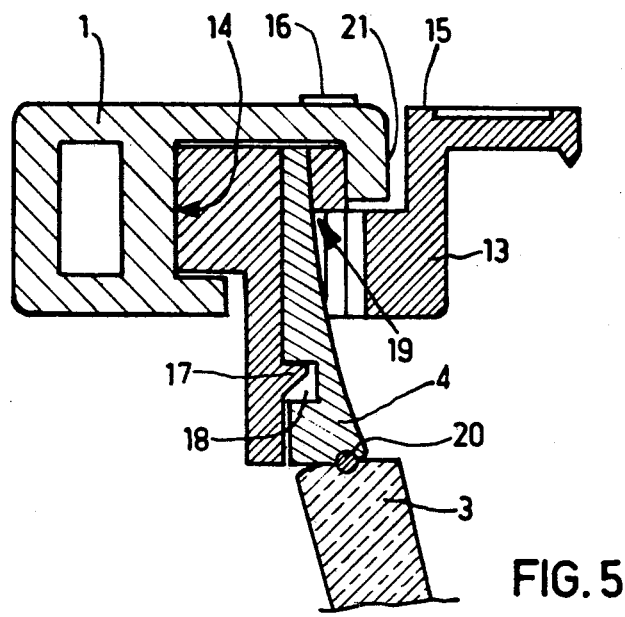
FIG. 5 is a sectional view of the lens carrier set in the groove of the mounting.

FIG. 5 is a section through one of lens carriers 13 which slides in a groove 14 of mounting 1. This carrier 13 comprises an index 15 which allows fixing of its position by reference marks or gradations (see FIG. 1) which are provided in mounting 1. The carrier 13 has a catch 17 which allows locking of the lens holder 4 by engagement of a groove 18 in said lens holder with the catch 17 after having conducted the upper part of lens holder 4 in a seat 19 of carrier 13. Test lenses 3 are attached to lens holder 4 by any convenient means, such as a clamp 20.

When a patient wants to undergo a testing of his vision with lenses according to the invention, the first adjustment carried out is the regulation of the height of removable holding piece 7 relative to the patient's nose or the regular eye glasses he continues to wear during testing. This adjustment requires only vertically adjusting and moving adjustable support 6 by exerting a pressure on the face 21, which is located on the front side of the frame. Leaf 8 is deformed by engaging face 9 of bar 5, and the conjugate bevel faces 10 and 11 are disengaged to allow the vertical sliding of support 6 on the section of bar 5 up to the desired position that can be marked on the vertical gradations of bar 5 and/or support 6. As soon as the wearer releases pressure on the face 21, support 6 is firmly immobilized in position by the wedging of faces 10 and 11.

Thereafter the wearer carries out the adjustment of the position of each of lenses 3 by making each of carriers 13 slide in its groove 14, whose friction is sufficient to hold in it place. By providing each carrier 13 with a device (not shown) for allowing the rotation of each lens around its optical axis, it is possible to adjust each lens 3 in rotation to take the orientation of the possible cylindrical axis of each lens into account.

As can be seen in FIG. 5, grooves 14 in which carrier 13 slides, are partly hidden inside the area of mounting 1 by the exterior frontal portion 21 of said mounting. The esthetic appearance of the novel eye glass unit is improved by rounded edges of different pieces and the avoidance of protrusions by providing, for example, screws with countersunk heads, such as, for example, fixing screw 12 of removable holding piece 7 which is provided with two holding arms, connected by a central positionable rod 22 and each carrying at its end a holding plate 23 for the nose.

Figure 3A:
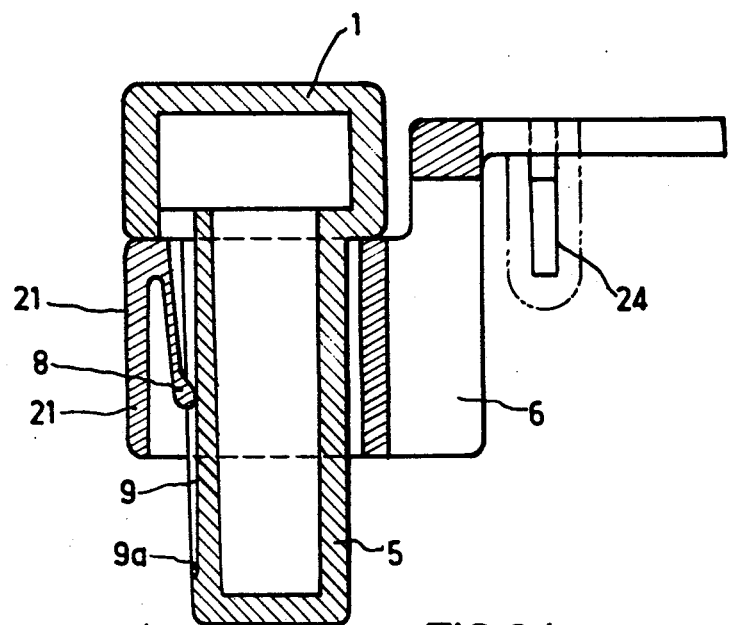
FIG. 3A is the same view showing a modification of the adjustable support.

FIG. 3A also shows that elastic leaf 8 of the adjustable support can engage a lower lug 9a of face 9 to prevent the adjustable support from escaping from bar 5 during adjustment. The modification of support 6 according to FIG. 3A is used for a patient who wears his regular eye glasses during testing. In this modification, special lugs 24 are provided on support 6 to maintain the position of lenses 3 upon changing the test eye glasses.

The invention is not limited to the embodiments shown and described, but covers all modifications thereof.

I claim:

1. Eye glasses for experimentation and testing of the type comprising a frame on which adjustable lens holders are shifted to allow eye testing of a patient to be provided with eye glasses having different corrective lenses, and with different positions of said lenses relative to the eyes of the patient, with said frame comprising a frontal mounting provided with two eye glass sidepieces and on which slide, in a longitudinally adjustable manner, two lens carriers, and the mounting is extended downwardly in its central portion in the direction of the patient's nose by a bar of short length and on which slides a vertically adjustable support, adapted to engage the patient's nose or the eye glasses he must wear during the test, characterized in that said bar (5) has a portion with two non-parallel faces (10) which form a wedging bevel and on which two conjugate faces (11) of the adjustable support (6) engage under the action of an elastic means (8) to maintain the adjustable support (6) in position by wedging.

2. Eye glasses according to claim 1, characterized in that the elastic means is a spring (8), the wedging action of which can be suppressed by the operator's hand proceeding to adjust the position of the support.

3. Eye glasses according to claim 2, characterized in that the spring in an elastic leaf (8) which is integral with the support (6) and is adapted to engage one face (9) of the section of the bar (5) in such a way that the patient who is proceeding to adjust the support, can, by pressure onto said support, suppress the wedging of the support (6) on the non-parallel faces (10) of the bar (5).

4. Eye glasses according to claim 3, characterized in that the leaf (8) is an element made by being cast in one piece with the support (6), manufactured from relatively elastic material like plastic material.

5. Eye glasses according to one of claims 1 to 4, characterized in that the support (6) comprises means of attachment (12) for holders to engage the nose or the frame of the eye glasses already worn by the patient.

6. Eye glasses according to one of claims 1 to 4, characterized in that the carriers (13) each slide in a groove (14), hidden at least partly inside the mounting (1), and in that the adjustable support (6) is provided with rounded edges on all its outer surfaces in such a manner as to make sure that the patient's esthetic comfort is assured and he is encouraged to wear the eye glasses for an extended test.

* * * * *